United States Patent
Klopp et al.

(10) Patent No.: US 7,511,170 B2
(45) Date of Patent: Mar. 31, 2009

(54) PROCESS FOR LIQUID/SOLID REACTION

(75) Inventors: Ingo Klopp, Weisenheim (DE); Thomas Bogenstätter, Bad Dürkheim (DE); Dirk Franke, Ludwigshafen (DE); Manfred Munzinger, Dirmstein (DE)

(73) Assignee: BASF Aktiengellschaft, Ludwigshafen (DE)

( * ) Notice: Subject to any disclaimer, the term of this patent is extended or adjusted under 35 U.S.C. 154(b) by 743 days.

(21) Appl. No.: 10/487,214

(22) PCT Filed: Aug. 29, 2002

(86) PCT No.: PCT/EP02/09659

§ 371 (c)(1),
(2), (4) Date: Feb. 19, 2004

(87) PCT Pub. No.: WO03/020411

PCT Pub. Date: Mar. 13, 2003

(65) Prior Publication Data

US 2004/0204605 A1 Oct. 14, 2004

(30) Foreign Application Priority Data

Aug. 29, 2001 (DE) ................. 101 42 284

(51) Int. Cl.
*C07C 63/06* (2006.01)
(52) U.S. Cl. .............. 562/405; 562/400; 422/261; 422/267
(58) Field of Classification Search ........... 562/400, 562/405; 422/261, 267
See application file for complete search history.

(56) References Cited

U.S. PATENT DOCUMENTS

| 3,075,830 | A | | 1/1963 | Schoenbeck et al. |
| 3,397,876 | A | * | 8/1968 | Valle .................. 266/170 |
| 4,956,176 | A | * | 9/1990 | Moorman .............. 426/478 |
| 2003/0004370 | A1 | * | 1/2003 | Wulff et al. ............ 562/18 |

FOREIGN PATENT DOCUMENTS

EP  0 471 550  2/1992

OTHER PUBLICATIONS

Chemiker-Zeitung 107 (1983), No. 4, pp. 121-126, Bollmacher, H. and Satori, P.

* cited by examiner

*Primary Examiner*—Daniel M Sullivan
*Assistant Examiner*—Sudhakar Katakam
(74) *Attorney, Agent, or Firm*—Novak Druce + Quigg LLP

(57) ABSTRACT

A process for carrying out a liquid/solid reaction comprises
  a) preparing a reaction suspension in which a first reactant is present in suspended form and a second reactant is present in dissolved form in a suspension medium, where one of the reaction products is insoluble in the suspension medium,
  b) passing the reaction suspension through an elongated reaction zone so that the Reynolds number of the stream is less than 20,000 and
  c) separating off the insoluble reaction product formed.

Figure 1:
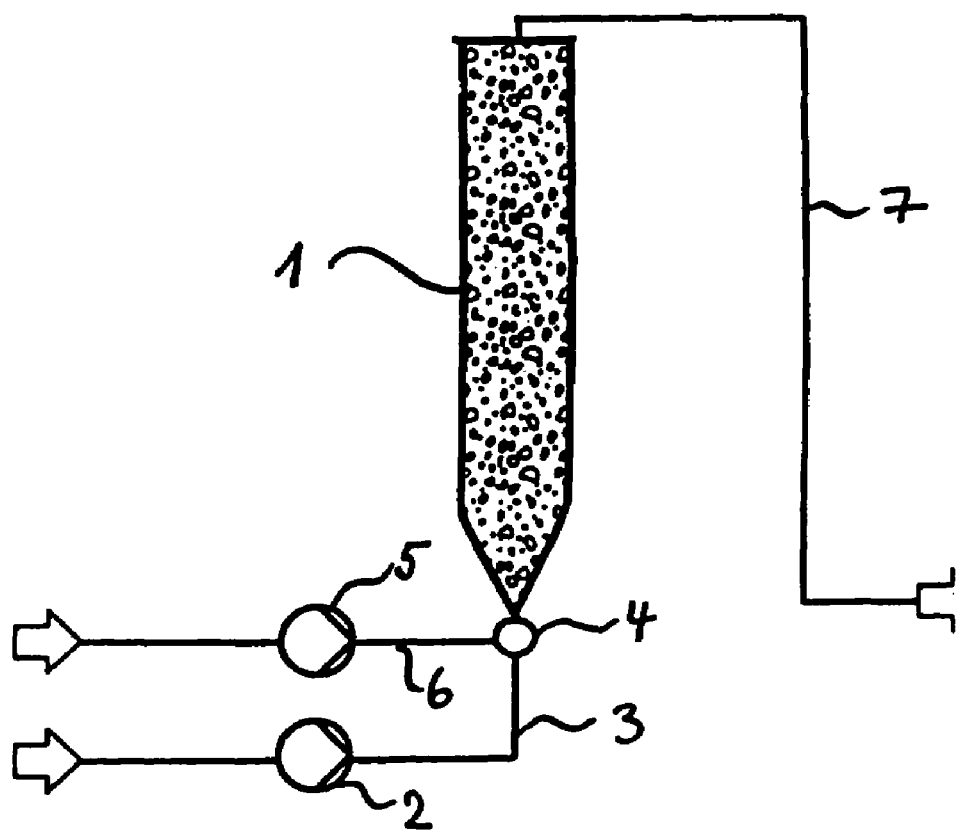

The process has the advantage that the insoluble reaction product is obtained in a readily filterable form.

12 Claims, 1 Drawing Sheet

PROCESS FOR LIQUID/SOLID REACTION

The present invention relates to a process for carrying out a solid/liquid reaction, i.e. a reaction in a liquid medium in which a first reactant is present in particulate, solid form and a second reactant is present in dissolved form and one of the reaction products is insoluble in the reaction medium. Appropriate choice of the reaction medium enables numerous reactions to be carried out in this way, e.g. the preparation of ethers or esters by the Williamson synthesis or the preparation of mixed acid anhydrides by reaction of a salt of a first acid with the halide of a second acid. The inorganic salt formed as coproduct in these syntheses is insoluble in many organic solvents.

An industrially important example is the reaction of sodium benzoate or ammonium benzoate with phosphorus (III) chloride to form tribenzoyl phosphite and sodium or ammonium chloride. Tribenzoyl phosphite can be reacted with triscyanomethylhexahydrotriazine and the reaction product can be hydrolyzed to N-phosphonomethylglycine, which is known under the name glyphosate and is a widely used total herbicide. Before the abovementioned further reaction of the tribenzoyl phosphite is carried out, it is necessary for all of the sodium or ammonium chloride formed to be separated off.

In Chemiker-Zeitung 107 (1938), No. 4, pp. 121-126, Bollmacher, H. and Satori, P. describe the preparation of tribenzoyl phosphite. Here, sodium benzoate is suspended in anhydrous ether and admixed with phosphorus(III) chloride. The solvent is subsequently distilled off in a high vacuum and by-products formed are removed by treatment with hexane.

In reactions of the type described, in which one reactant is a solid while the other reactant is present as a solution in the liquid phase, the reaction takes place at the surface or in the immediate vicinity of the surface of the solid reactant. The insoluble reaction product is formed on the surface of the solid reactant. However, the contact points between the initially charged solid reactant and the solid reaction product which is formed are extremely fragile. Furthermore, the volume of the solid reactant steadily decreases during the course of the reaction, so that only a loose agglomerate of the solid reaction product is present at the end of the reaction. The solid reaction product growing on the surface of the solid reactant frequently forms porous structures which are likewise quite fragile. Even small mechanical stresses are sufficient to detach the solid reaction product from the surface of the solid reactant or to destroy the loose agglomerate of the solid reaction product. Intensive stirring during the reaction leads to formation of very fine and thus difficult-to-filter solids. These disadvantages become increasingly pronounced as the batch size increases, since abrasion is increased in large batches as a result of the higher shear at the stirrer. However, without mechanical mixing, the solids would settle at the bottom of the reaction vessel or float at the surface of the liquid, which leads to an unacceptable lengthening of the reaction times due to the long diffusion paths.

It is an object of the present invention to provide a process for carrying out a solid/liquid reaction in which the insoluble reaction product is obtained in a readily filterable form.

We have found that this object is achieved by a process which comprises a) preparing a reaction suspension in which a first reactant is present in suspended form and a second reactant is present in dissolved form in a suspension medium, where one of the reaction products is insoluble in the suspension medium, b) passing the reaction suspension through an elongated reaction zone so that the Reynolds number of the stream is less than 20,000 and c) separating off the insoluble reaction product formed.

The suspension medium is chosen so that it is inert toward the reactants used and the reaction products. The first reactant is insoluble in the suspension medium, while the second reactant is soluble therein. The insoluble reaction product can be the target product or a coproduct of the reaction.

For the purposes of the present invention, "insoluble" means a solubility of less than 1 g/100 ml and "soluble" means a solubility or miscibility of more than 5 g/100 ml, each at the respective reaction temperature. The reaction suspension flows through the reaction zone at a Reynolds number of less than 20,000, preferably less than 10,000, particularly preferably less than 5,000, i.e. flow is substantially laminar or slightly turbulent. The reaction suspension is accordingly passed through the reaction zone under low-shear conditions. "Elongated reaction zone" means that the ratio of length to (longest) diameter of the reaction zone is more than 10, preferably more than 25. The cross section of the reaction zone is not critical, but a circular cross section is generally preferred.

The process of the present invention avoids, firstly, a situation where the fragile particles in the reaction suspension are subjected to excessive mechanical forces which lead to abrasion and undesirably fine solid. Secondly, the laminar or at most slightly turbulent flow prevents the occurrence of inhomogeneities in the reaction suspension, e.g. the settling of solids.

The reaction suspension is passed through the elongated reaction zone in a direction parallel to the longitudinal axis of the latter. In general, the longitudinal axis of the reaction zone is preferably vertical, i.e. the reaction suspension is passed through the reaction zone either in the direction of gravity or opposite to the direction of gravity. Flow in a direction opposite to that of gravity is preferred when the insoluble reaction product formed has a density higher than that of the suspension medium, while flow in the direction of gravity is preferred when the insoluble reaction product formed has a density lower than that of the suspension medium and/or the reaction is significantly exothermic, leading to a reduction in the density of the suspension medium during the reaction. The flow velocity should preferably be selected so that it is at least as great as the velocity at which the particles of the insoluble reaction product formed sink or float, which is in turn dependent on various factors, for example the viscosity of the reaction medium.

The first step of the process of the present invention is preparation of a "reaction suspension", i.e. a suitable, selected suspension medium, the first reactant and the second reactant are brought into contact and the reactants are homogeneously dispersed in the suspension medium. The reaction suspension typically has a solids content of from 10 to 50% by weight. An upper limit to the solids content is imposed merely by the need for the suspension to remain readily pumpable. On the other hand, working with highly dilute suspensions is not economical.

In the preparation of the reaction suspension, the order of addition of the reactants to the suspension medium is not critical per se. However, preference is generally given to preparing the reaction suspension by mixing a suspension of the first reactant in the suspension medium with the liquid or dissolved second reactant. Thus, a preferred procedure is to slurry the particulate first reactant in the suspension medium and to admix the resulting suspension with the second reactant, if it is liquid, or with a solution of the second reactant in the suspension medium or a solvent which is miscible therewith.

The addition of the liquid or dissolved second reactant is advantageously carried out by metering the second reactant into a stream of the suspension of the first reactant in a mixing zone upstream of the reaction zone. The mixing time in the mixing zone should be short compared to the residence time in the reaction zone. The residence time in the reaction zone is preferably at least 5 times, in particular at least 10 times, particularly preferably at least 20 times, the residence time in the mixing zone. The residence time in the reaction zone is typically from 2 minutes to 6 hours.

Effective mixing in of the second reactant can, for example, be achieved by means of static mixing elements which are located immediately downstream of the point at which the second reactant is metered in. However, a preferred method of mixing is to pass the suspension through the mixing zone at a high flow velocity and then to decrease the flow velocity. This is advantageously achieved by the part of the mixing zone located downstream of the point of addition having a larger cross section than the region of the point of addition. Owing to the low static pressure prevailing in the region of high flow velocity, the second reactant which has been metered in is intimately mixed with the flowing suspension. The flow velocity is subsequently decreased to obtain the low-shear conditions employed in the process of the present invention.

It is also possible to add the second reactant to the suspension of the first reactant at a plurality of points. Thus, for example, part of the second reactant can be added in a mixing zone upstream of the reaction zone and the remainder can be metered in at one or more points in the reaction zone.

The process of the present invention can be carried out adiabatically, i.e. without substantial heat exchange with the surroundings. On the other hand, it is possible to provide appropriate heat exchange elements for heating and/or cooling, e.g. pipe coils through which a heating or cooling medium flows and which are located in the wall of a flow tube serving as reaction zone or are located on the wall in such a way that heat is conducted between the wall and the coils. Internals through which a heating or cooling medium flows and which are located in the reaction zone are likewise possible, but owing to the risk of turbulence being generated are not preferred. The reaction temperature varies greatly with the type of reactants used. A general guideline range is from −80 to 250° C.

In many cases it is advantageous to divide the reaction suspension into a plurality of substreams and to pass the substreams through parallel tubes. The parallel tubes can be surrounded by a heat transfer medium, so that the process of the present invention can be carried out in a simple manner in a customary shell-and-tube heat exchanger.

The flow profile with which the reaction suspension moves through the reaction zone is essentially that of plug flow or is a parabolic profile. It is possible to improve radial mixing of the reactant suspension by means of suitable internals in the reaction zone. However, when deciding the shape and arrangement of the internals, care has to be taken to ensure that the low-shear character of the flowing stream is not adversely affected.

The insoluble reaction product formed is advantageously separated off by sedimentation or preferably by filtration. For this purpose, the suspension is preferably introduced directly, without passing through a transport device, into a filtration apparatus. Suitable filtration apparatuses are, for example, belt filters, rotary filters, filter presses or centrifuges. Preference is given to continuously operating filtration apparatuses, in particular belt filters.

Possible first reactants in the process of the present invention are, for example, salts of organic acids or oxygen-containing inorganic acids or alkoxides; possible second reactants are inorganic or organic acid halides and alkyl halides.

Suitable salts of organic or oxygen-containing inorganic acids are alkali metal, alkaline earth metal or ammonium salts of aliphatic, aromatic or heteroaromatic carboxylic acids or sulfonic acids. These include $C_1$-$C_{18}$-alkane carboxylic acids, e.g. formic acid, acetic acid or propionic acid, and also monocyclic or bicyclic aromatic carboxylic acids whose ring(s) may contain one or two hetero atoms selected from among nitrogen, oxygen and sulfur and which may bear from one to four substituents selected independently from among $C_1$-$C_4$-alkyl, $C_1$-$C_4$-alkoxy, nitro and halogen, e.g. benzoic acid, naphthoic acid or pyridinecarboxylic acid.

Suitable alkoxides are the alkali metal or alkaline earth metal salts of alcohols or phenols. Such alcohols or phenols include straight-chain or branched $C_1$-$C_{18}$-alkanols, e.g. methanol or ethanol, and also monocyclic or bicyclic aromatic hydroxy compounds which may be substituted as described above.

Among alkali metal salts, preference is generally given to the sodium and potassium salts. Particular preference is also given to the ammonium salts which can be derived from ammonia and amines. They include, for example, tetra-$C_1$-$C_{18}$-alkyl ammonium salts in which the alkyl radicals can be identical or different.

Suitable inorganic acid chlorides are, for example, phosphorus(III) chloride, phosphorus(V) chloride, thionyl chloride or sulfuryl chloride. Suitable organic acid chlorides are aliphatic, aromatic or heteroaromatic acid halides, in particular the chlorides. They include the halides of $C_1$-$C_{18}$-alkanecarboxylic acids and sulfonic acids, e.g. acetyl chloride, propionyl chloride or methanesulfonyl chloride, and also the halides of monocyclic or bicyclic aromatic carboxylic acids or sulfonic acids which may be substituted as described above, e.g. benzyl chloride, benzenesulfonyl chloride or p-toluenesulfonyl chloride.

Suitable alkyl halides are primary, secondary or tertiary alkyl chlorides, bromides or iodides. These include straight-chain or branched $C_1$-$C_{18}$-alkyl halides such as methyl chloride, ethyl chloride or tert-butyl chloride.

Suitable suspension media are aliphatic and aromatic hydrocarbons such as hexane, heptane, octane, isooctane, cyclohexane, methylcyclohexane, benzene, alkybenzenes having up to 3 $C_1$-$C_4$-alkyl radicals on the aromatic ring, e.g. toluene, o-, m- and p-xylene and mixtures thereof; halogenated hydrocarbons, in particular chlorinated hydrocarbons, e.g. dichloromethane, trichloromethane, 1,2-dichloroethane, 1,1,2-trichloroethane, chlorobenzene, perchloroethylene, 1,2-dichloropropane; fluorinated hydrocarbons such as fluorobenzene or fluoroalkyl-substituted benzenes; ethers, such as diethyl ether, diisopropyl ether, dioxane, tetrahydrofuran, dimethoxyethane, diethylene glycol dimethyl ether; ketones such as acetone, cyclohexanone, methyl isobutyl ketone; or esters such as ethyl acetate; organic nitro compounds such as nitromethane or nitrobenzene.

The suspension medium is preferably used in essentially water-free form, i.e. the water content of the suspension medium is preferably less than 0.5% by weight, in particular less than 0.1% by weight.

The invention is illustrated by the accompanying figure and the examples below.

FIG. 1 schematically shows an apparatus suitable for carrying out the process of the present invention. Details which are not necessary for an understanding and are self-evident per se have been left out.

A suspension of a solid reactant in a suspension medium is fed to the reaction zone 1 by the pump 2 and the line 3. A liquid or dissolved second reactant is brought via the pump 5 and the line 6 and metered in via a mixing nozzle 4. The suspension leaving the reaction zone is discharged via line 7 and passed to a filtration apparatus.

EXAMPLES

Example 1

A suspension of ammonium benzoate in dichloroethane (20% by weight) was fed at a rate of 2000 g·h$^{-1}$ to the bottom of a vertical flow tube having a length of 150 cm and a diameter of 3 cm. At the same time, 131.5 g·h$^{-1}$ of phosphorus (III) chloride were metered into the suspension via a T-piece upstream of the inlet of the flow tube. The ammonium benzoate suspension was precooled to 6-7° C., while the phosphorus(III) chloride was at room temperature. The reaction mixture passed through the tube in plug flow at a Reynolds number of less than 2000. The temperatures were 31° C. at the bottom (about 5 cm after the addition of phosphorus(III) chloride) and 36° C. in the mixture which flowed over the top. The mixture which flowed over the top was filtered through a pressure filter. The benzoic acid content of the filtrate after hydrolysis with acetonitrile/water was found to be 17.0% by weight, and the chloride content was found to be less than 0.32% by weight. The filter resistance of the ammonium chloride was $3.8 \cdot 10^{12}$ mPa·s·m$^{-2}$.

Example 2

A suspension of ammonium benzoate in dichloroethane (24.2 g in 100 ml) was fed at a rate of 25.6 ml/min to the bottom of the flow tube described in Example 1. At the same time, 7.72 ml/min of a 20% strength by weight solution of phosphorus(III) chloride in dichloroethane were metered into the suspension via a T-piece upstream of the inlet of the flow tube. The reaction mixture flowed through the tube in plug flow. The temperature about 5 cm after the addition of phosphorus(III) chloride was 38° C. The mixture which flowed over at the top was filtered through a pressure filter. About 33.3 g/min of filtrate were obtained. The benzoic acid content of the filtrate after hydrolysis with acetonitrile/water was found to be 14.2% by weight. The filter resistance of the ammonium chloride was $4.9 \cdot 10^{12}$ mPa·s·m$^{-2}$.

Comparative Example 3

3127 g of a 20% strength ammonium benzoate solution were placed in a stirred vessel fitted with a double impeller stirrer at 15° C. and 226.8 g of phosphorus(III) chloride were added dropwise over a period of 45 minutes. The stirrer ran at 80 rpm. The mixture was stirred for another 40 minutes at 15-18° C. The mixture was subsequently filtered through a pressure filter. The filter resistance of the ammonium chloride was $2\text{-}2.5 \cdot 10^{13}$ mPa·s·m$^{-2}$. After hydrolysis with water/acetonitrile, the filtrate was found to contain 17.4% by weight of benzoic acid.

We claim:

1. A process for carrying out a liquid/solid reaction which comprises
   a) preparing a reaction suspension in which a first reactant selected from among salts of organic and oxygen-containing inorganic acids and alkoxides is present in suspended form and a second reactant selected from among inorganic and organic acid halides and alkyl halides is present in dissolved form in a suspension medium, where one of the reaction products is insoluble in the suspension medium,
   b) passing the reaction suspension through an elongated reaction zone so that the Reynolds number of the stream is less than 20,000, wherein the longitudinal axis of the reaction zone is vertical and the reaction suspension is passed through the reaction zone opposite to the direction of gravity, and
   c) separating off the insoluble reaction product formed by filtration.

2. A process as claimed in claim 1, wherein the Reynolds number of the stream is less than 10,000.

3. A process as claimed in claim 1, wherein the reaction suspension is prepared by mixing a suspension of the first reactant in the suspension medium with the liquid or dissolved second reactant.

4. A process as claimed in claim 3, wherein the residence time of the reaction suspension in the reaction zone is at least 10 times the mixing time.

5. A process as claimed in claim 3, wherein the second reactant is metered into a stream of the suspension of the first reactant.

6. A process as claimed in claim 5, wherein the flow velocity of the suspension is decreased after the second reactant has been metered into it.

7. A process as claimed in claim 1, wherein the reaction suspension is divided into a plurality of substreams and the substreams are conveyed through parallel tubes.

8. A process as claimed in claim 7, wherein the parallel tubes used are surrounded by a heat transfer medium.

9. A process as claimed in claim 1, wherein the suspension medium is selected from among hydrocarbons, halogenated hydrocarbons, ethers, ketones and esters.

10. A process as claimed in claim 9, wherein the suspension medium is selected from among 1,2-dichloroethane, 1,2-dichloropropane and mixtures thereof.

11. A process as claimed in claim 1, wherein the first reactant used is an alkali metal salt or the ammonium salt of benzoic acid and the second reactant used is phosphorus (III) chloride.

12. A process as claimed in claim 1, wherein the reaction suspension has a solids content of from 10 to 50% by weight.

* * * * *